United States Patent [19]
Sausa et al.

[11] Patent Number: 5,906,946
[45] Date of Patent: *May 25, 1999

[54] DEVICE AND PROCESS FOR DETECTING AND DISCRIMINATING NO AND $NO_2$ FROM OTHER NITROCOMPOUNDS IN REAL-TIME AND IN SITU

[75] Inventors: Rosario C. Sausa, Bel Air; Robert Pastel, Aberdeen, both of Md.

[73] Assignee: United States of America as represented by the Secretary of The Army, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/700,713

[22] Filed: Aug. 5, 1996

[51] Int. Cl.$^6$ .......................... G01N 21/01; G01N 33/22
[52] U.S. Cl. .................... 436/116; 250/282; 436/106; 436/107; 436/117; 436/118; 436/173
[58] Field of Search .................. 436/116–118, 106, 436/107, 173, 183; 250/282

[56] References Cited

U.S. PATENT DOCUMENTS

| | | |
|---|---|---|
| 5,094,815 | 3/1992 | Conboy et al. . |
| 5,123,274 | 6/1992 | Carroll et al. . |
| 5,128,882 | 7/1992 | Cooper et al. . |
| 5,316,950 | 5/1994 | Apitz et al. . |
| 5,364,795 | 11/1994 | Sausa et al. . |

OTHER PUBLICATIONS

F. Lahmani et al. *J. Phys. Chem.* 1985, 89, 5646–5649.
P. Marcus et al. *Int. J. Mass Spectrum. Ion Processes* 1988, 82, 319–333.
A. Clark et al. *Sens. VI 6th* 1993, 57–61.
A Marshall et al. *Analyst* 1994, 119, 1719–1724.
K.W.D. Ledingham *Phys. Scr. T* 1995, T58, 100–103.
R.J.S. Morrison et al. *J. Chem. Phys.* 1982, 77, 5994–6004.
A.M. Angus et al. *Opt. Commun.* 1975, 14, 223–225.
T. Ebata et al. *Chem. Phys. Lett.* 1982, 89, 45–47.
T.G. Slanger et al. *J. Chem. Phys.* 1983, 79, 2231–2240.
M.O. Rodgers et al. *Environ. Sci Technol.* 1989, 23, 1106–1112.
G.A. Bruker et al. *Chem. Phys Lett.* 1992, 194, 301–308.
D.C. Robie et al. *Chem. Phys. Lett.* 1992, 193, 413–422.
G.W. Lemire et al. *Anal. Chem.* 1993, 65, 529–533.
A. Clark et al. *Analyst* 1993, 118, 601–607.
A. Marshall et al. *Rapid Commun. Mass Spectrum.* 1994, 8, 521–526.
D.B. Galloway et al. *J. Chem. Phys.* 1994, 100, 1946–1952.
J.B. Simeonsson et al. *Anal. Chem.* 1994, 66, 2272–2278.
T. Benter et al. *Fresenius J. Anal. Chem.* 1995, 351, 489–492.
M. Hippler et al. *Chem. Phys. Lett.* 1995, 243, 500–505.
K.W.D. Ledingham *Rapid Commun. Mass Spectrum.* 1995, 9, 1522–1527.
J.B. Simeonsson et al. *Appl. Spectrosc. Rev.* 1996, 31, 1–72.
R.L. Pastel et al. *Appl. Opt.* 1996, 35, 4046–4052.

*Primary Examiner*—Arlen Soderquist
*Attorney, Agent, or Firm*—Paul S. Clohan; U. John Biffoni

[57] ABSTRACT

The excitation of the target nitrocompound with ultraviolet radiation results in photodissociation yielding vibrationally excited NO with significant population of the v"=1 and v"=2 levels of the ground electronic state. As the population distribution of ambient NO favors the v"=0 level, discrimination between vibrationally excited NO and ambient NO is possible by probing the NO A–X (0,0),(1,1), and (2,2) bands near 226, 224, and 222 nm, respectively, employing (1+1) resonance-enhanced multiphoton ionization (REMPI). Many complex nitrocompounds cannot be photolyzed near 452 nm since their absorption cross sections are relatively small. Thus, the visible laser radiation is used to facilitate the detection of ambient NO and NO from $NO_2$ by (2+2) REMPI and to discriminate these species from more complex nitrocompound analytes. The analytical utility of the present invention has been demonstrated at several photolysis/ionization wavelengths for $NO/CH_3NO_2$ and $NO_2/CH_3NO_2$ mixtures. Limits of detection have also been determined for NO, $NO_2$, nitromethane ($CH_3NO_2$), nitrobenzene ($C_6H_5NO_2$) diethylglycoldinitramine (DEDGN), and trinitrotoluene (TNT), and are in the ppb to ppm range.

25 Claims, 4 Drawing Sheets

DEVICE AND PROCESS FOR DETECTING AND DISCRIMINATING NO AND NO$_2$ FROM OTHER NITROCOMPOUNDS IN REAL-TIME AND IN SITU

FIELD OF THE INVENTION

The invention is directed to a device and process for detecting and discriminating NO and NO$_2$ by photodissociation with a laser having a two-color output.

RELATED APPLICATIONS

U.S. Pat. application Nos. 08/744,704 (Attorney Docket No. 96-13) and 08/680,080 (Attorney Docket No. 97-17), filed concurrently herewith and entitled respectively "HAND-HELD PROBE FOR REAL-TIME ANALYSIS FOR TRACE POLLUTANTS IN ATMOSPHERE AND ON SURFACE" and "SENSOR AND METHOD FOR DETECTING TRACE UNDERGROUND ENERGETIC MATERIALS", disclose related subject matter. The disclosure of these applications is hereby incorporated by reference.

DESCRIPTION OF THE RELATED ART

Environmental and security concerns have urgently motivated the detection and monitoring of trace amounts of nitrocompounds such as propellants, explosives and nitropollutants.

Common techniques used for the detection and discrimination of NO and NO$_2$ from nitrocompounds include infrared absorption, laser infrared differential absorption radar (LIDAR), quadruple mass spectrometry, and ion mobility spectrometry. These techniques are relatively slow (minutes) and the apparatuses are bulky. The infrared techniques also suffer from low sensitivity and interference from other naturally abundant infrared absorbers such as H$_2$O. Although ion mobility spectrometry is a sensitive and relatively fast technique (seconds), it is not so accurate as other techniques, since the signal dependence on concentration is nonlinear. Moreover, the technique suffers from clustering of the target molecules with water and competition for protonation with contaminates.

U.S. Pat. No. 5,123,274 to Carroll et al describes a device for analyzing explosives. The target molecules are first collected, separated with a gas chromatograph, and then pyrolyzed yielding NO as one of the major endproducts. NO is detected by chemiluminescence. Related to this invention is U.S. Pat. No. 5,094,815 to Conboy and Hotchkiss which discloses an apparatus which uses a photolytic interface for HPLC. NO is cleaved from non volatile N-nitroso compounds by photolysis using a mercury vapor lamp, separated from the solvent through a series of cold traps, and then carried by helium gas into a reaction chamber for chemiluminescence detection. The response time of these inventions is in the order of minutes, making them impractical for large sample operations, i.e. baggage inspection at a busy airport.

Recently, Sausa et al of the U.S. Army Research Laboratory developed an apparatus and method for the sensitive detection of nitrocompounds including energetic materials. Selected references include: (1) U.S. Pat. No. 5,364,795 to Sausa, Simeonsson, and Lemire, entitled Laser-based detection of nitro-containing compounds and (2) Simeonsson, Lemire, and Sausa, "Trace Detection of Nitrocompounds" by ArF Laser Photofragmentation/Ionization Spectrometry, *Applied Spectroscopy,* Vol. 47, No. 11, p. 190, 1993. The technique is based on laser photofragmentation/fragment detection spectrometry and employs one laser to both photofragment the target molecule and facilitate detection of the characteristic NO photofragment. Using a laser operating near 226 nm, NO is detected by resonance-enhanced multiphoton ionization (REMPI) or laser induced fluorescence (LIF) via its $A^2\Sigma - X^2\Pi$ transitions near 226 nm, while using an ArF laser, NO is detected by REMPI processes via the NO $A^2\Sigma - X^2\Pi$ (3,0) $B^2\Pi - X^2\Pi$ (7,0), and $D^2\Sigma - X^2\Pi$ (1,0) bands at 193 nm. In both cases the analytical utility is demonstrated for several compounds using time-of-flight mass spectrometry that employs a molecular beam. The use of laser ionization with time-of-flight mass spectrometry allows for the detection and discrimination of NO and NO$_2$ from nitrocompounds based on the time of arrival of the ions at the detector. Although the sensor has a high sensitivity and fast response time, its utility in the field is limited due to the size of the mass spectrometer.

More recently, Simeonsson, Lemire, and Sausa published an article titled "Laser-Induced Photofragmentation/Photoionization Spectroscopy: A Method for Detecting Ambient Oxides of Nitrogen," *Analytical Chemistry,* Vol. 66, No. 14, p. 2272, 1994. The method utilized a tunable laser operating near 226 nm. The NO ions which were generated subsequent to the photolysis of the target molecule were detected using a pair of miniature electrodes. As the apparatus measures a signal representing a total NO quantity, it cannot discriminate NO and NO$_2$ from the target nitrocompound. The ability to discriminate these species from more complex nitrocompounds is important, particularly in field use, since NO and NO$_2$ are atmospheric pollutants which will contribute to the background noise.

SUMMARY OF THE INVENTION

An object of the invention is to provide a device and method for discrimination of NO and NO$_2$ from complex nitrocompounds in real time and in situ.

Another object is to provide such a device and method which are accurate and reliable, which have a fast response time, and which can be used for monitoring trace nitrocompounds in air or on various surfaces.

Yet another object is to provide such a device and method in which the sensor is rugged and capable of field use.

To these and other ends, the present invention employs a sensor having a frequency agile laser, such as one with output in the regions of 444–555 and 222–227 nm. The ultraviolet radiation is generated by frequency doubling the output radiation in the visible. The UV-visible laser radiation serves multiple functions. First, it is used to photodissociate the target nitrocompound molecule producing the characteristic NO photofragment. Second, it facilitates the discrimination of ambient NO from fragment NO. Because the NO fragment is formed vibrationally excited, it can be distinguished from ambient NO by probing the NO A–X (0,0), (1,1) and (2,2) bands near 226, 224, and 222 nm, respectively, using (1+1) REMPI. Complex nitrocompounds are fragmented more efficiently by UV radiation compared to visible radiation since their absorption cross-section increases with shorter wavelength. Thus, the visible radiation is used to detect and discriminate possible NO and NO$_2$ interferents by (2+2) REMPI via the NO A–X (0,0), (1,1) and (2,2) bands. These species have relatively large visible REMPI responses compared to the target nitrocompounds molecules.

The present invention has been shown to be useful and has been demonstrated on a number of nitrocompounds such as nitromethane (CH$_3$NO$_2$), nitrobenzene (C$_6$H$_5$NO$_2$), diethylglycoldinitramine (DEDGN), and trinitrotoluene (TNT).

The present invention utilizes laser photofragmentation/fragment ionization using UV and visible radiation to discriminate NO and $NO_2$ from more complex nitrocompounds. Discrimination of the species is achieved by monitoring the difference of UV and visible ionization response of ambient NO, NO produced from the photolysis of $NO_2$, and NO generated from the photolysis of the nitrocompounds using the NO A–X (0,0), (1,1), and (2,2) bands.

In this way, the present invention can discriminate between species by monitoring their photodissociation efficiencies at various wavelengths as well as their internal energy distributions.

The excitation of many energetic material and nitropollutants by radiation in the region of 190–250 nm results in the formation of vibrationally excited NO, $X^2\Pi$ ($v'' \geq 1$). The population distribution of ambient NO, however, favors the ground vibrational state, $X^2\Pi$ ($v''+0$). Thus, both fragment and ambient NO are readily detected with a high degree of sensitivity and selectivity by REMPI via their A–X (0,0), (1,1), or (2,2) bands. The interaction of visible radiation with the target nitrocompound molecules does not result in photofragmentation since most nitrocompounds have relatively low absorptions in the visible. As a result, many nitrocompounds lack a REMPI response using visible radiation. In contrast, ambient NO and $NO_2$ have large REMPI responses from visible laser radiation. Thus, NO and $NO_2$ can be discriminated from more complex nitrocompounds because of the difference of nitrocompound photofragmentation efficiency with UV and visible laser radiation and the difference in REMPI response with visible radiation.

The UV-visible laser photodissociation and fragment detection technique of the invention is most effective when coupled with ion detection. Ion detection can have nearly 100% collection efficiency and is independent of fluorescence transition strength inherent in the LIF detection method. After ionization, all the ions can be easily directed to the collection plates by an electric field formed from the parallel plates. In contrast, LIF detection suffers from the exited molecules emitting in many frequencies and directions.

The apparatus described herein is employed in the following fashion. The detection head, composed of a pair of collection plates and lens assembly coupled to one end of a fiber optic, is brought to the point of interest where vapors of the analyte are sampled. UV or visible laser radiation which is transmitted through the fiber optic is then focused in the center of the collection plates. The sample vapor is photofragmented and the characteristic NO fragment subsequently photoionized. An electric field, produced by applying a 40–600 V difference on the collection plates, directs the ions to one of the potential plates. The ion current is converted to voltage by a transimpedance amplifier and then directed into a gated integrator or a digital oscilloscope for real-time display. A laptop computer (or other suitable computing device) interfaced to the boxcar or oscilloscope is used for data acquisition and analysis. In the case of NO and $NO_2$ discrimination from more complex nitrocompounds, the sample vapor is interrogated at three frequencies in the VU or visible. A simple and fast computation performed on the signals from the three interrogated frequencies determines the concentration of each NO, $NO_2$, and target nitrocompound. These calculations can be performed by a programmable microprocessor. (or other suitable computing device).

BRIEF DESCRIPTION OF THE DRAWINGS

The preferred embodiment of the invention will now be described in detail with reference to the drawings, in which.

DETAILED DESCRIPTION OF THE PREFERRED EMBODIMENT

Figure 1:
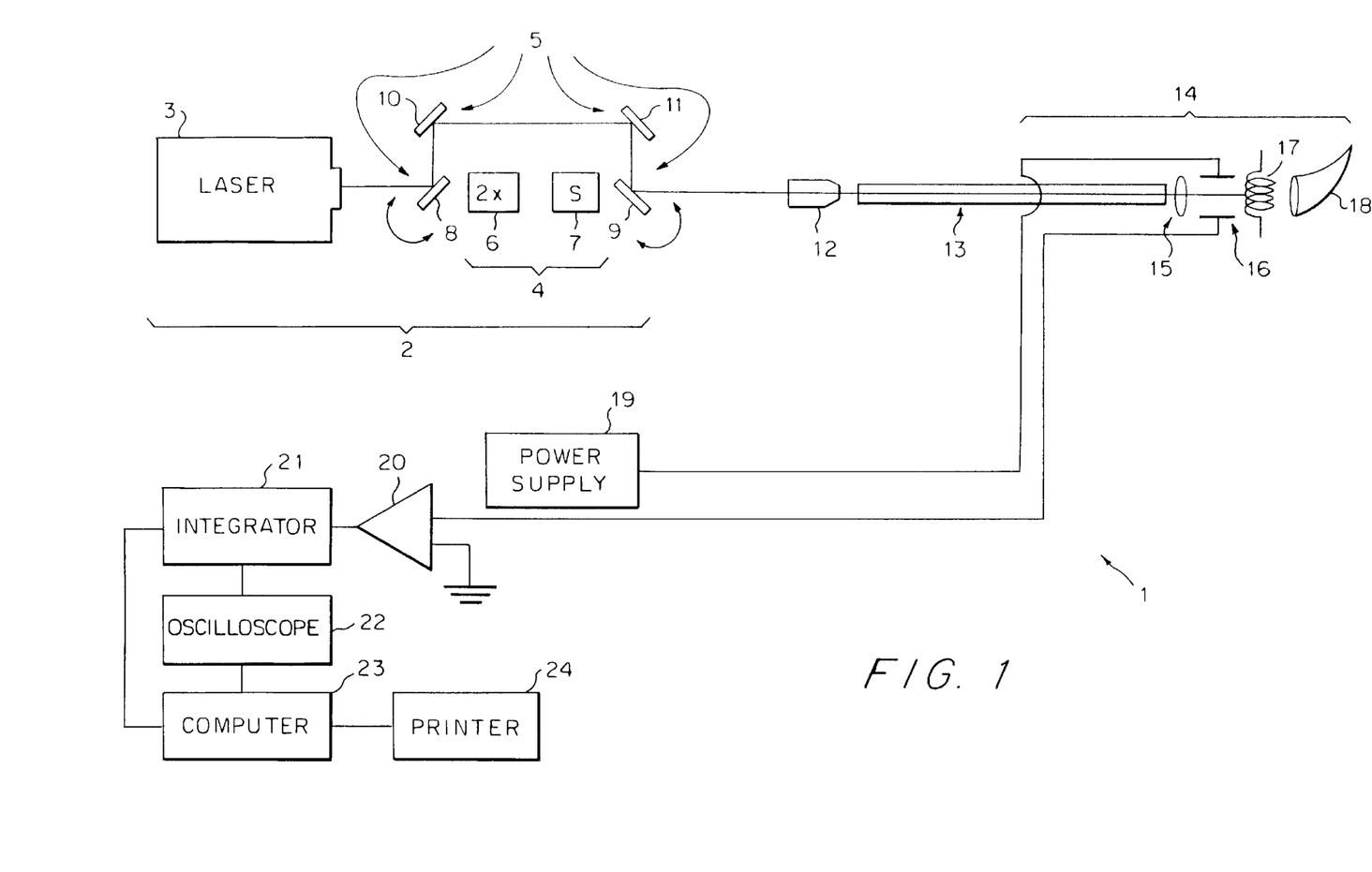
FIG. 1 shows a schematic diagram of the experimental apparatus.

FIG. 1 is a schematic diagram of trace nitrocompound analyzer 1 within the preferred embodiment of the present invention. Central to analyzer 1 is the UV-visible frequency agile laser system 2. The laser system includes tunable visible laser 3, frequency doubling unit or module 4, and a set of four mirrors 5. An optical parametric oscillator or frequency doubled Ti: sapphire could also be used in place of pulsed dye laser 3. Frequency doubling module 4 includes doubling crystal 6 and chromatic separator 7. Set of mirrors 5 redirects the visible laser radiation away from the frequency doubling module 4 when measurements are made in the visible range. Mirrors 8 and 9 are synchronously rotated to accomplish the redirection. Mirrors 8 and 9 can be replaced by Bragg cells or by an assembly of a polarizer, an electro-optic crystal, and a polarization sensitive reflector. The UV or visible laser radiation is focused into one end of optical fiber 13 by lens system 12. Detection of the nitrocompounds with NO and $NO_2$ background subtraction is accomplished at the detector head 14 which comprises, at the other end of the optical fiber 13, lens system 15 for focusing the laser radiation between the electrodes 16, heater coil 17, and beam stop 18. For compounds with a relatively high vapor pressure, the laser radiation is used to photolyze the target molecules and ionize the characteristic NO photofragment. For solid compounds which have a low vapor pressure at room temperature, vaporization and/or decomposition of the sample is accomplished with the same laser radiation or a heater coil. In all cases, the ions produced by REMPI are then collected by electrodes 16. One plate of the electrode pair is biased to 40–400 V by power supply 19, while the other plate is connected to transimpedance amplifier 20. Transimpedance amplifier 20 converts the ion current to voltage and the resulting signal is sampled and averaged by boxcar integrator 21 or displayed on digital oscilloscope 22. Laptop computer 23 (or another suitable computing device) interfaced to boxcar 21 and oscilloscope 22 is used for data acquisition and analysis. For hard copies of the data, printer 24 is connected to the computer.

Figure 2:
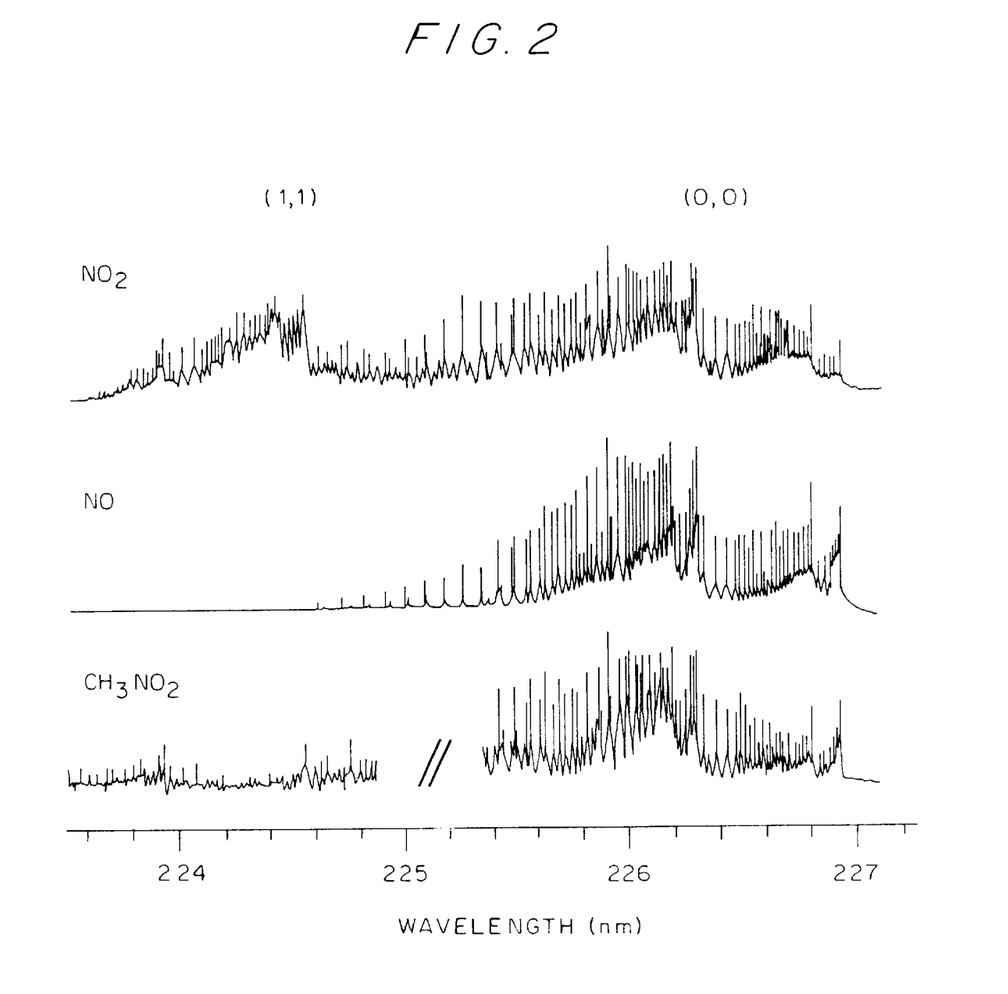
FIG. 2 shows REMPI spectra of ambient NO, NO generated from $NO_2$, and NO generated from $CH_3NO_2$.
Figure 3A:
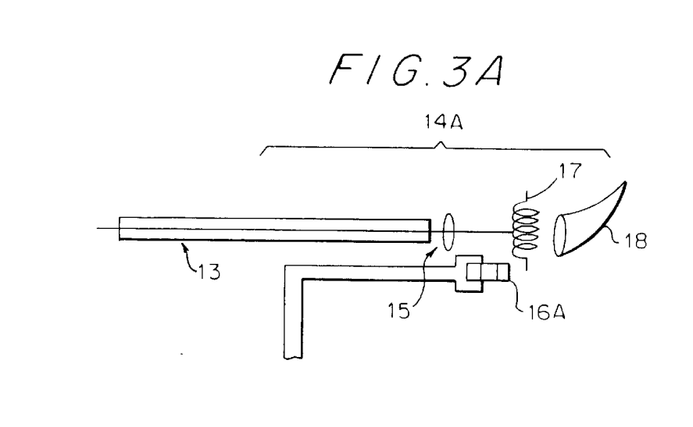
FIGS. 3A–3E show variations of the apparatus shown in FIG. 1.
Figure 3B:
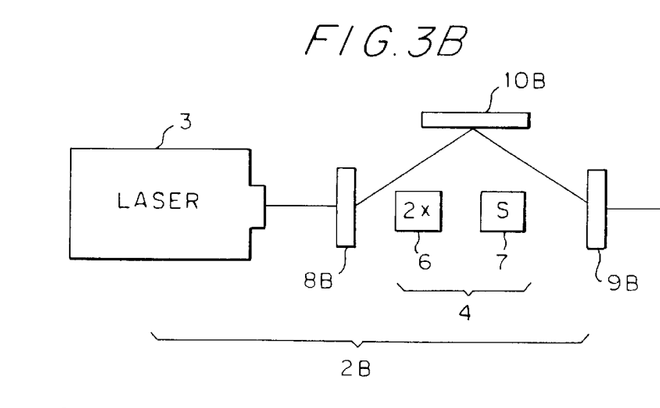
Figure 3C:
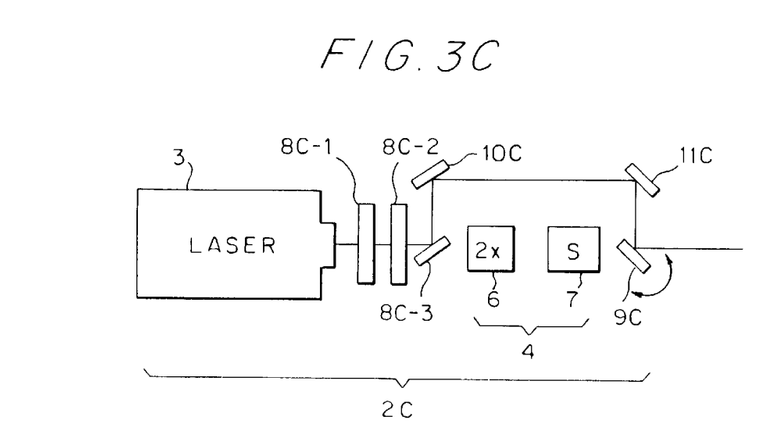
Figure 3D:
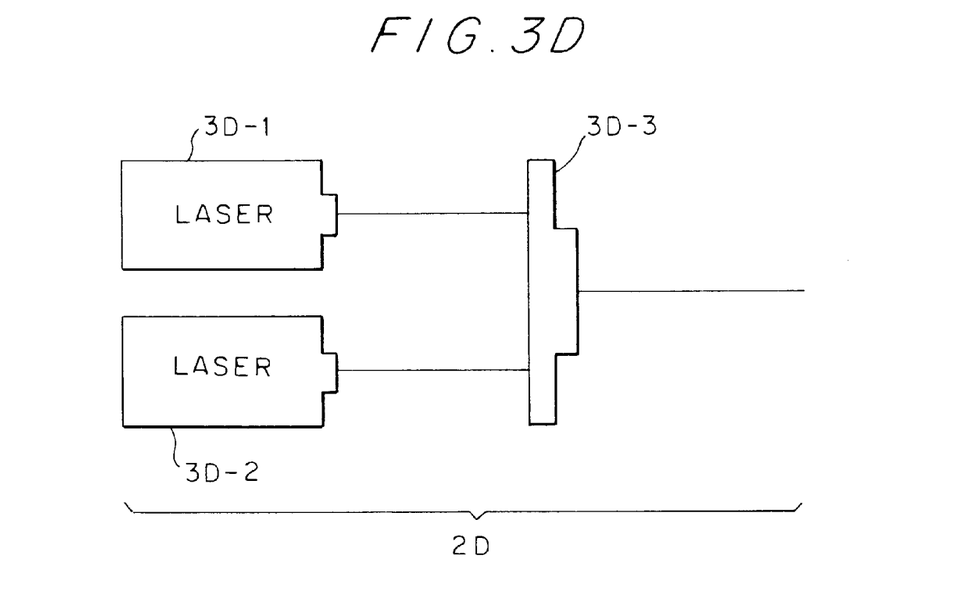
Figure 3E:
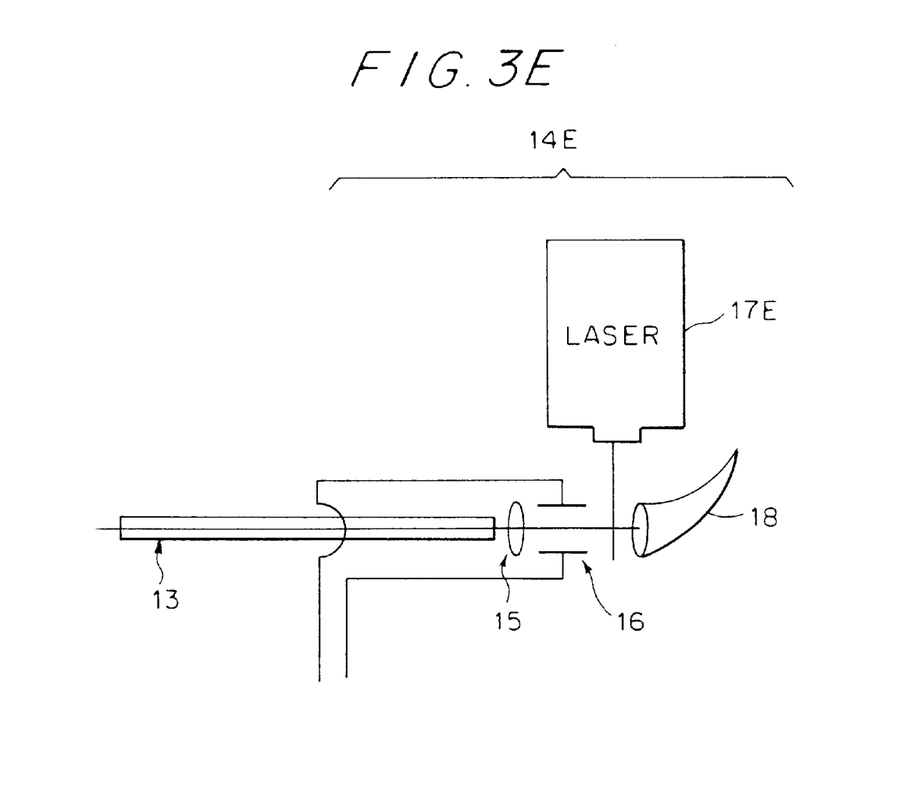

FIG. 2 shows a REMPI spectrum in the region of 223.5–227 nm of ambient NO, NO produced from $NO_2$, and NO produced from nitromethane. The spectra were recorded at 100 Torr with the laser operating at 10 Hz and a scan speed of 0.005 nm/sec, and with 3 shot averaging. An increase in spectral recording is possible by operating the pump laser at higher repetition rates (100–200 Hz) which are readily attainable from commercially available excimer lasers. The unique features of the spectra and rotational resolution reveal that the present invention can be highly selective based on wavelength excitation. The features near 226 and 224 nm are associated with NO A–X (0,0) and (1,1) transitions. Also observed, but not shown, are NO A–X (2,2) transitions near 222 nm. Similar spectra of nitrobenzene, diethylglycoldinitramine,(DEDGN), and trinitrotoluene (TNT) have been recorded and their REMPI response measured at various wavelengths.

The ionization signal dependence on species concentration was investigated for various target molecules at several UV and visible wavelengths, and was observed to be linear over a range of 3–4 decades. Tables 1 and 2 below are tables comparing the responses of NO, NO$_2$, nitromethane, nitrobenzene, DEGDN, and TNT for REMPI detection at several UV and visible wavelengths, respectively. As shown in the tables, the complex nitrocompounds, R—NO$_2$, have a relatively small REMPI response to visible excitation wavelengths compared to UV excitation wavelengths, while NO and NO$_2$ have large REMPI responses to both the UV and visible wavelengths. This permits the discrimination of NO and NO$_2$ from R—NO$_2$ by comparing the UV and visible ionization response. Thus, the quantitative analysis of NO, NO$_2$, and R—NO$_2$ is accomplished by selecting two visible excitation wavelengths such as 450.7 and 449.2 nm for detecting an discriminating NO and NO$_2$, and a third ionization wavelength in the UV such as 226.3 or 223.9 nm for detecting the nitrocompound. The signals from all three ionization wavelength are then interpreted simultaneously to determine the concentration of NO, NO$_2$, and more complex nitrocompound.

TABLE 1

REMPI RESPONSE (mV/ppm)

| SPECIES | 454.3 nm | 450.7 nm | 449.2 nm | 443.1 nm |
|---|---|---|---|---|
| NO | 22.57 | 41.82 | 0.27 | 0.15 |
| NO$_2$ | 19.85 | 20.01 | 10.6 | 8.84 |
| CH$_3$NO$_2$ | 5.0 × 10−4 | 7.0 × 10−4 | 1.0-10−4 | — |
| C$_6$H$_5$NO$_2$ | 1.0 × 10−2 | 7.0 × 10−2 | 1.0 × 10−3 | 8.0 × 10−4 |
| DEDGN | 4.7 × 10−3 | 5.8 × 10−3 | 1.8 × 10−3 | — |
| TNT | — | — | — | — |

TABLE 2

REMPI RESPONSE (mV/ppm)

| SPECIES | 226.3 nm | 223.9 nm | 222.2 nm |
|---|---|---|---|
| NO | 779 | 4.5 | 5.3 |
| NO$_2$ | 46 | 19.3 | 6.5 |
| CH$_3$NO$_2$ | 6.8 | 4.2 | 2.4 |
| C$_6$H$_5$NO$_2$ | 1.4 | 1.4 | — |
| DEDGN | 0.96 | 0.30 | 0.20 |
| TNT | 0.63 | — | — |

The total ion signal from a mixture of NO, NO$_2$, and nitrocompound, R—NO$_2$, at radiation wavelength, λ, is due to the sum of the response from ambient NO, NO produced from NO$_2$ photolysis, and NO generated from R—NO$_2$ photolysis. The signal may be expressed as $$S(\lambda) = R_{NO}(\lambda)[NO] + R_{NO2}(\lambda)[NO_2] + R_{R-NO2}(\lambda)[R-NO_2] \quad (1)$$

where $R_{NO}(\lambda)$ is the ambient NO ionization response from λ laser ionization, $R_{NO2}(\lambda)$ is the response of fragment NO from NO$_2$ photolysis, and $R_{R-NO2}(\lambda)$ is the response of fragment NO from R—NO$_2$ photolysis. The sample is interrogated at three wavelengths, at least one of which is in the UV range. This generates a set of three equations and three unknowns:

$$S(\lambda_1) = R_{NO}(\lambda_1)[NO] + R_{NO2}(\lambda_1)[NO_2] + R_{R-NO2}(\lambda_1)[R-NO_2]$$

$$S(\lambda_2) = R_{NO}(\lambda_2)[NO] + R_{NO2}(\lambda_2)[NO_2] + R_{R-NO2}(\lambda_2)[R-NO_2] \quad (2)$$

$$S(\lambda_3) = R_{NO}(\lambda_3)[NO] + R_{NO2}(\lambda_3)[NO_2] + R_{R-NO2}(\lambda_3)[R-NO_2]$$

The responses of the three compounds at the three excitation wavelengths are measured separately during the calibration of the instrument and stored in RAM. The matrix $$R = \begin{bmatrix} R_{NO}(\lambda_1) & R_{NO2}(\lambda_1) & R_{R-NO2}(\lambda_1) \\ R_{NO}(\lambda_2) & R_{NO2}(\lambda_2) & R_{R-NO2}(\lambda_2) \\ R_{NO}(\lambda_3) & R_{NO2}(\lambda_3) & R_{R-NO2}(\lambda_3) \end{bmatrix} \quad (3)$$

can be inverted prior to the measurements and also stored in RAM. The signals:

$$S = \begin{bmatrix} S(\lambda_1) \\ S(\lambda_2) \\ S(\lambda_3) \end{bmatrix} \quad (4)$$

can be multiplied by $R^{-1}$s to determine the concentrations of NO, NO$_2$, and R—NO$_2$.

The choice of ionization wavelengths affects the error in calculating the absolute concentration and in determining the proper scaling of the signals. To demonstrate these effects, we consider two sets of three ionization wavelengths, 450.7, 449.2 and 223.9 nm, and 450.7, 449.2, and 226.3 nm. From tables 1 and 2, a coefficient matrix for the set of excitation wavelength 450.7, 449.2, and 223.9 nm with unit mV/ppm is given by, $$R = \begin{bmatrix} 41.8 & 20.0 & 0.0007 \\ 0.27 & 10.6 & 0.0001 \\ 4.5 & 19.3 & 4.2 \end{bmatrix} \quad (5)$$

The conditional number of R is:

$$\text{cond}(R) = \|R\| \, \|R^{-1}\| = 40.6 \quad (6)$$

where $\|R\|$ is the norm of the matrix R. In the above case we have used the row norm defined by:

$$\|R\| = \max_{1 \leq i \leq n} \sum_{j=1}^{n} |a_{ij}| \quad (7)$$

Mathematically, the inverse conditional number is the relative distance of the closest singular (non-invertible) matrix and reveals how the error propagates through the system. For example, if Δs represents the error in measuring the signals, then $$\|\Delta x\|/\|x\| \leq \text{cond}(R) \, \|\Delta\|/\|s\| \quad (8)$$

is the relative error of determining the concentrations. In other words, the conditional number scales the relative error in the signal to the relative error in calculating and measuring the concentrations. The conditional number is always greater than or equal to unity. It is equal to one only for diagonal matrixes. In the above set of excitation wavelengths, cond(R)=40.6. This value is acceptable, guaranteeing that the relative error in measuring the signal is amplified at most by an order of magnitude.

The matrix coefficient of the second set of excitation wavelengths, 450.7, 449.2, and 226.3 nm is given by $$R = \begin{bmatrix} 41.8 & 20.01 & 0.0007 \\ 0.270 & 10.6 & 0.0001 \\ 779 & 46 & 6.8 \end{bmatrix} \quad (9)$$

and cond(R)=6,258. This value is unacceptably large. The coefficient matrix in equation (9) suffers from poor scaling since the matrix element $r_{3,1}=779$ dominates the norm. Scaling R, using diagonal matrixes K and L, yields $$R' = KRL \quad (10)$$

$$= \begin{bmatrix} 1 & 0 & 0 \\ 0 & 1 & 0 \\ 0 & 0 & 0.1 \end{bmatrix} \begin{bmatrix} 41.8 & 20.1 & 0.00007 \\ 0.270 & 10.6 & 0.0001 \\ 779 & 46 & 6.8 \end{bmatrix} \begin{bmatrix} 0.1 & 0 & 0 \\ 0 & 0.1 & 0 \\ 0 & 0 & 1 \end{bmatrix}$$

$$= \begin{bmatrix} 4.18 & 2.001 & 0.070 \\ 0.027 & 1.06 & 0.001 \\ 7.79 & .460 & 1.480 \end{bmatrix}$$

As shown in equation (10) matrix R' does not have a dominant element. Calculating cond(R') yields an acceptable value of 80.5. The absolute concentrations of NO, $NO_2$ and $CH_3NO_2$ can be determined from:

$$x = L(KR'L)^{-1}Ks \quad (11)$$

where the scaling compensates for the large response of NO and $NO_2$ at all frequencies and the large response of all compounds in the UV range.

The range of measurable mixtures of $CH_3NO_2$ in the presence of NO and $NO_2$ is determined from the species's response and signal noise. For $CH_3NO_2$ in the presence of NO, we assume that the bulk of the signal is due to the presence of NO. The calculated concentration of $CH_3NO_2$ required to exceed three times the signal noise of the system is given by $$R_{CH3NO2}(\lambda)\,[CH_3NO_2]/R_{NO}(\lambda)\,[NO]=\Delta S/S \geq 3N \quad (12)$$

where N is the relative noise of the system. Most of the system signal noise is due to variation in laser pulse energy, E. The laser energy varies by approximately 10%, so that $(\Delta E/E)n^{-1/2}=0.01$, where n is the number of laser pulses for which results are averaged and n=100 (in an illustrative example) Then, $$(\tfrac{1}{3}N_{NO})\,\{R_{CH3NO2}(\lambda)/R_{NO}(\lambda)\} > [NO]/[CH_3NO_2] \quad (13)$$

determines the maximum $[NO]/[CH_3NO_2]$ ratio.

The mixture $NO/CH_3NO_2$ can only be determined as long as NO can be detected in the presence of $CH_3NO_2$. Using an analysis similar to that described above, but exchanging the role of NO and $CH_3NO_2$ ($S=R_{CH3NO2}(\lambda)\,[CH_3NO_2]$ and $\Delta S=R_{NO}(\lambda)\,[NO]$), yields the minimum $[NO]/[CH_3NO_2]$ ratio that can be measured, $$[NO]/[CH_3NO_2] \geq 3N_{CH3NO2}\{R_{CH3NO2}(\lambda)/R_{NO}(\lambda)\} \quad (14)$$

At the laser intensities employed in our apparatus, the $CH_3NO_2$ ion signal dependence on laser pulse energy is approximately cubic. Therefore, $N_{CH3NO2}=(3\Delta E/E)\,n^{-1/2}$.

Inequalities (13) and (14) reveal that the range of $[NO]/[CH_3NO_2]$ that can be calculated is determined solely by the signal noise of the system. It should be noted that the lowest concentration of $CH_3NO_2$ in the presence of a very small quantity of NO is not determined by either inequality (13) and (14). Using a similar analysis for $CH_3NO_2$ and $NO_2$ mixtures yields their mixture range.

Table 3 below is a table showing the range of measurable $NO/CH_3NO_2$ and $NO_2/CH_3NO_2$ mixtures at 223.9 and 226.3 nm determined from inequalities (13) and (14). The range is approximately three decades for both mixtures and wavelengths. In the case of $NO/CH_3NO_2$ mixture, the 223.9 nm wavelength is more suited for measuring the larger ratio of $[NO]/[CH_3NO_2]$ while the 226.3 nm wavelength is more suited for measuring the smaller ratio of $[NO]/[CH_3NO_2]$. It is noted that below the $[NO]/[CH_3NO_2]$ lower limit detection, $CH_3NO_2$ can be detected ignoring the NO response.

TABLE 3

RANGE OF MEASURABLE $NO/CH_3NO_2$ AND $NO_2/CH_3NO_2$ MIXTURES

| | NO | | | $NO_2$ | | |
|---|---|---|---|---|---|---|
| | $R_{CH3NO2}/R_{NO}$ | $[NO]/[CH_3NO_2]$ Maximum | $[NO]/[CH_3NO_2]$ Minimum | $R_{CH3NO2}/R_{NO2}$ | $[NO_2]/[CH_3NO_2]$ Maximum | $[NO_2]/[CH_3NO_2]$ Minimum |
| 226.3 nm | $8.7 \times 10^{-3}$ | 0.29 | $7.8 \times 10^{-4}$ | 0.15 | 2.47 | 0.013 |
| 223.9 nm | 0.92 | 30.74 | $8.3 \times 10^{-2}$ | 0.22 | 3.60 | 0.020 |
| Noise | — | 0.01 | 0.03 | — | 0.02 | 0.03 |

Presented in Tables 4 and 5 below are limits of detection of NO, $NO_2$ and more complex nitrocompounds. The limits of detection are reported as the concentration equal to three times the standard deviation of the background noise evaluated in the absence of the analyte molecule from 20 independent measurements, each the average of 100 laser pulses. As shown in the table, the limits of detection range from low ppb for NO and $NO_2$ to low ppm for the complex nitrocompounds.

TABLE 4

| | Visible REMPI Limits of Detection (ppm) | | | |
|---|---|---|---|---|
| | 454.3 nm | 450.7 nm | 449.2 nm | 443.1 nm |
| NO | 0.010 | 0.006 | 0.75 | 1.3 |
| $NO_2$ | 0.011 | 0.013 | 0.019 | 0.023 |
| $CH_3NO_2$ | 438 | 373 | 2000 | — |
| $C_6H_5NO_2$ | 22 | 3.7 | 200 | 250 |
| DEDGN | 47 | 45 | 113 | — |
| TNT | — | — | — | — |

TABLE 5

| | UV REMPI Limits of Detection (ppm) | | |
|---|---|---|---|
| | 226.3 nm | 223.9 nm | 222.2 nm |
| NO | 0.002 | 0.120 | 0.1 |
| $NO_2$ | 0.032 | 0.028 | 0.08 |
| $CH_3NO_2$ | 0.20 | 0.13 | 0.23 |
| $C_6H_5NO_2$ | 1.1 | 0.38 | — |
| DEDGN | 1.5 | 1.8 | 2.7 |
| TNT | 2.3 | — | — |

FIGS. 3A–3E show variations in the structure of the analyzer. For example, in detector head 14A shown in FIG. 3A, electrodes 16 may be replaced by multichannel plate 16A. In laser system 2B of FIG. 3B, set of mirrors 5 is replaced by Bragg cells 8B, 9B and fixed mirror 10B, while in laser system 2C of FIG. 3C, set of mirrors 5 is replaced by polarizer 8C-1 for imparting a polarization to the laser beam, electro-optic crystal 8C-2 for selectively rotating the polarization imparted by the polarizer, polarization selective mirror 8C-3 and fixed mirrors 10C, 11C and 9C. In laser system 2D of FIG. 3D, two lasers 3D-1 and 3D-2 output pulses of different frequencies to beam combiner 3D-3; frequency doubling module 4 and set of mirrors 5 are dispensed with. In detector head 14E of FIG. 3E, heater coil 17 is replaced by second laser 17E for volatilizing the sample. Of course, more than one of these variations may be applied to the apparatus.

While the preferred embodiment of the invention has been disclosed, those skilled in the art who have reviewed this application will readily appreciate that modifications may be mode within the scope of the invention. For example, the wavelengths may be varied as needed. Therefore, the invention is to be construed as limited only by the appended claims.

What is claimed is:

1. A sensor for detecting and discriminating NO and $NO_2$ from more complex nitrocompounds in a sample in real-time and in situ, said sensor comprising:

(a) pulsed laser means emitting three different wavelength laser beams, all of said laser beams having wavelengths in the visible or ultraviolet regions with at least one beam from each region, said beams producing ions from the sample;

(b) detecting means for detecting the ions to produce a detection signal; and (c) data acquisition and analysis means receiving said detection signal for determining and discriminating a presence and a concentration of the NO, $NO_2$ and nitrocompounds in the sample.

2. A sensor as in claim 1, further comprising a detection head including a lens means, wherein the pulsed laser means comprises a pulsed laser for emitting the laser pulses, fiber optic means for conveying the laser pulses from the pulsed laser to the detection head and lens means, said lens means for receiving the laser pulses from the fiber optic means and for causing the laser pulses to be incident on the sample.

3. A sensor as in claim 2, wherein the detecting means is disposed in the detection head.

4. A sensor as in claim 3, wherein the detection head further comprises a heater coil for heating the sample to volatilize the sample.

5. The sensor of claim 3, wherein the detection head further comprises second laser means for heating the sample to volatilize the sample.

6. A sensor as in claim 2, wherein the detection head further comprises a beam stop disposed in a path of the laser pulses on a side of the detecting means remote from the lens means.

7. A sensor as in claim 1, wherein the detecting means comprises an ion detector for detecting $NO_+$ species, and wherein the ion detector comprises a multichannel plate.

8. A sensor as in claim 1, wherein the pulsed laser means comprises:

a single laser for emitting visible laser light in the 444–454.3 nm wavelength region;

frequency doubling means, receiving the visible laser light from the laser, for selectively doubling a frequency of the visible laser light; and a chromatic separator for separating a first portion of the visible laser light whose frequency has been doubled by the frequency doubling means and a second portion of the visible laser light whose frequency has not been doubled by the frequency doubling means.

9. A sensor as in claim 8, wherein the frequency doubling means comprises a frequency doubling crystal and redirecting means for selectively redirecting the visible laser light from the laser onto the frequency doubling crystal.

10. A sensor as in claim 9, wherein the redirecting means comprises at least one rotating mirror.

11. A sensor as in claim 9, wherein the redirecting means comprises at least one Bragg cell.

12. A sensor as in claim 9, wherein the redirecting means comprises:

a polarizer, receiving the visible laser light from the laser, for imparting a polarization to the visible laser light;

an electro-optic crystal, receiving the visible laser light polarized by the polarizer, for selectively rotating the polarization; and a polarization sensitive reflector, receiving the visible laser light from the electro-optic crystal.

13. A sensor as in claim 1, wherein said laser means comprises:

first laser for producing laser pulses in said visible wavelength region; and a second laser, separate from the first laser, for producing laser pulses in said ultraviolet wavelength region.

14. The sensor of claim 1, wherein said visible wavelength region comprises 444–454.3 nm wavelengths and said ultraviolet region comprises 222–227 nm wavelengths.

15. The sensor of claim 1, wherein said laser means emits two laser beams having wavelengths in the visible region and one laser beam having a wavelength in the ultraviolet region.

16. The sensor of claim 15, wherein said visible wavelengths are selected from the group consisting of 454.3, 450.7, 449.2 and 443.1 nm, and said ultraviolet wavelength is selected from the group consisting of 226.3, 223.9 and 222.2 nm.

17. The sensor of claim 15, wherein said laser beams have wavelengths of 450.7, 449.2 and 223.9 nm.

18. The sensor of claim 15, wherein said laser beams have wavelengths of 450.7, 449.2, and 226.3 nm.

19. A method for detecting and discriminating NO and $NO_2$ from more complex nitrocompounds in a sample in real-time and in situ, comprising the steps of:

(a) exciting the sample using three different wavelength laser beams, all of said beams having wavelengths in the visible or ultraviolet regions with at least one beam from each region, wherein said beams produce ions;

(b) detecting ion response to the excitation to produce a detection signal; and (c) determining and discriminating a presence and a concentration of the NO, $NO_2$ and nitrocompounds in the sample in accordance with the detection signal.

20. The method of claim 19, wherein step (a) comprises using multiple laser beams to photodissociate the nitrocompounds, and wherein step (b) comprises detecting internal energy distributions of NO from the nitrocompounds, NO dissociated from $NO_2$, and the NO in the sample by REMPI.

21. The method of claim 19, wherein said visible wavelength region comprises 444–454.3 nm wavelengths and said ultraviolet region comprises 222–227 nm wavelengths.

22. The method of claim 19, wherein said three different wavelength laser beams comprises two laser beams having wavelengths in the visible region and one laser beam having a wavelength in the ultraviolet region.

23. The method of claim 22, wherein said visible wavelengths are selected from the group consisting of 454.3, 450.7, 449.2 and 443.1 nm wavelengths, and said ultraviolet wavelength is selected from the group consisting of 226.3, 223.9, and 222.2 nm wavelengths.

24. The method of claim 22, wherein said laser beams have wavelengths of 450.7, 449.2 and 223.9 nm.

25. The method of claim 22, wherein said laser beams have wavelengths of 450.7, 449.2, and 226.3 nm.

* * * * *